United States Patent [19]

Szarvasi et al.

[11] 4,190,665

[45] Feb. 26, 1980

[54] SUBSTITUTED ARYLALIPHATIC ACIDS

[75] Inventors: Etienne Szarvasi, Charbonnieres-Les Bains; Didier Festal, Ecully, both of France

[73] Assignee: Lipha, Lyonnaise Industrielle Pharmaceutique, Lyon, France

[21] Appl. No.: 855,361

[22] Filed: Nov. 28, 1977

[30] Foreign Application Priority Data

Nov. 30, 1976 [FR] France ................ 76 35993

[51] Int. Cl.$^2$ ................ A61K 31/40; C07D 207/24
[52] U.S. Cl. ................ 424/274; 260/326.41
[58] Field of Search ................ 424/274; 260/326.41

[56] References Cited

U.S. PATENT DOCUMENTS

| | | | |
|---|---|---|---|
| 3,579,535 | 5/1971 | Denss et al. | 260/326.41 |
| 3,868,391 | 2/1975 | Carney et al. | 260/326.41 |
| 3,993,763 | 11/1976 | Carney et al. | 260/326.41 |

FOREIGN PATENT DOCUMENTS

| | | |
|---|---|---|
| 4244M | 6/1966 | France . |
| 2035026 | 8/1974 | France . |
| 2059527 | 10/1975 | France . |
| 488695 | 5/1970 | Switzerland . |
| 504434 | 4/1971 | Switzerland . |
| 1299172 | 12/1972 | United Kingdom . |

*Primary Examiner*—Stanley J. Friedman
*Attorney, Agent, or Firm*—Browdy and Neimark

[57] ABSTRACT

Substituted arylaliphatic acids represented by the general formula

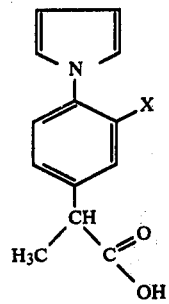

wherein X is a nitro or amino group, may be used as drugs, in particular as an analgesic and anti-inflammatory agent.

8 Claims, No Drawings

SUBSTITUTED ARYLALIPHATIC ACIDS

The present invention relates to substituted arylaliphatic acids and their preparation and application. Numerous substituted arylacetic acids are described and are active as analgesics and anti-inflammatory agents.

It has been found that a combination of particularly intense activity and low toxicity can be obtained when the aryl residue of the molecule is substituted in the 4 position by a 1-pyrrolyl residue, and in the 3 position by a nitro or preferably an amino group.

The new compounds are represented by the formula

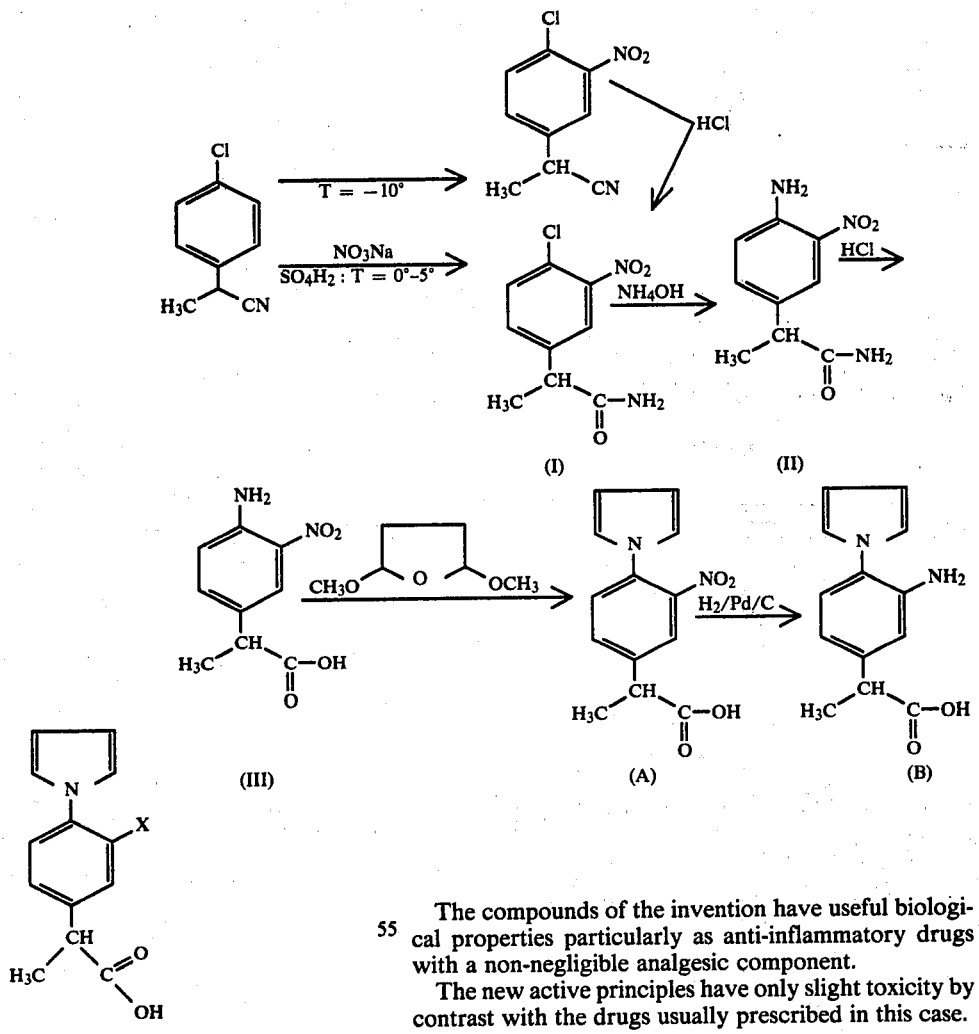

wherein X is a nitrogenous substituent chosen from the nitro or amino groups.

The process for preparing the products of the present invention consists of nitrating 2-(4'-chlorophenyl) propionitrile.

According to the operating conditions relating to the nitration temperature, one obtains directly either the corresponding nitrated amide in the 3' position, or the nitrile, nitrated in the same position. Nitration is preferably carried out with the intermediary of an alkaline nitrate in an acid solution between 0° and 5° C. to obtain the amide directly, and at about −10° C. in the second case.

In the latter case, the nitrile is later hydrolyzed into amide with the aid of hydrochloric acid.

By an original process, 2-(4'-chloro-3'-nitro-phenyl) propionamide (I), thus obtained, is treated with ammonia in an alcohol solution to furnish 2-(4'-amino-3'-nitro-phenyl) propionamide (II) which, when hydrolyzed in an acid medium, is transformed into 2-(4'-amino-3'-nitro-phenyl) propionic acid (III). This, when treated with 2,5-dimethoxytetrahydrofuran (a mixture of cis-/trans isomers) produces 2-(3'-nitro-4'-[1''-pyrrolyl] phenyl) propionic acid (A). Catalytic hydrogenation of the latter in the presence of palladium on activated charcoal produces 2-(3'-amino-4'-[1''-pyrrolyl] phenyl) propionic acid (B).

The synthesis takes place as follows:

The compounds of the invention have useful biological properties particularly as anti-inflammatory drugs with a non-negligible analgesic component.

The new active principles have only slight toxicity by contrast with the drugs usually prescribed in this case.

| Active principle | LD$_{50}$, orally, mouse |
|---|---|
| 2-(3'-nitro-4'-[1''-pyrrolyl]phenyl) propionic acid (compound A) | 3200 mg/kg |
| 2-(3'-amino-4-[1''-pyrrolyl] phenyl) propionic acid (compound B) | 3000 mg/kg |

The anti-inflammatory effect of the new drugs was determined in two tests.

(a) In the carrageenin-induced edema test according to Winter, C. A. and Risley, E. A. (*Proc. Soc. Exp. Biol. Med.* 1962, 111, 544–547) the protection conferred by the drug administered orally to the rat against an edema triggered by injecting a carrageenin suspension into the sole of the foot of the rat was investigated. The table below gives the "active dose 30" (inhibiting edema development by 30%) of both compounds.

| Active principle | AD₃₀ orally |
|---|---|
| Compound A | 12 mg/kg |
| Compound B | 12 mg/kg |

(b) In the UV erythema test on the guinea pig (Winder, C. V., Wax, J., Burr, V., Been, M., Rosiere, C. E., *Arch. Int. Pharmacodyn.*, 116, 261, 1958) the protective activity against precocious inflammation in the albino guinea pig was investigated. A determination was made of the active dose 50 which, administered orally to the animal, decreased erythema (produced by exposure to ultraviolet radiation) of the shaved back of the guinea pig by 50%.

| Active Principle | Active Dose 50 |
|---|---|
| Compound A | 18.4 mg/kg |
| Compound B | 4.7 mg/kg |

The analgesic activity can be determined in the mouse by the method of Koster, R., Anderson, M., Debeer, E. J., *Federation Proc.*, 1959, 18, 412. A determination was made of the active dose 50 of the drug which, administered orally, diminished painful contractures, caused by intraperitoneal injection of a dilute acetic acid solution, by 50%.

| Active Principle | Active Dose 50 |
|---|---|
| Compound A | 50 mg/kg |
| Compound B | 19 mg/kg |

Therapeutic compositions containing the compound according to the present invention as the active principle are effective as anti-inflammatory and analgesic agents at daily doses between 200 and 600 mg.

Pharmaceutical compositions can be presented in the form of tablets, suppositories, ointments, and syrups.

Formulation Example:

| Sugar-coated pills: | |
|---|---|
| Active principle | 100 mg |
| Lactose | 30 mg |
| Wheat starch | 29 mg |
| Talc | 10 mg |
| Gelatin | 5 mg |
| Alginic acid | 20 mg |
| Fecula | 5 mg |
| Magnesium stearate | 1 mg |
| a tablet of | 200 mg |

Suppositories with 250 mg active principle may also be formulated in known manner.

Examples are given hereinbelow of the preparation of compounds illustrating the invention in a nonlimitative manner.

EXAMPLE 1

(2-(4'-chloro-3'-nitro-phenyl) propionamide

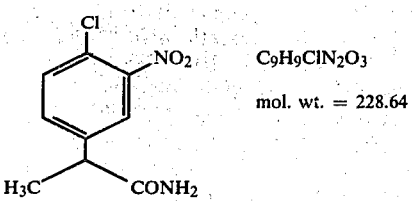

$C_9H_9ClN_2O_3$ mol. wt. = 228.64

Prepared:

(a) directly by simultaneous nitration and hydrolysis of 2-(4'-chloro-phenyl) propionitrile, according to the process of R. I. Meltzer (*J. Org. Chem.* 26, 1418 (1961)).

(b) by hydrochloric acid hydrolysis of 2-(4'-chloro-3'-nitro-phenyl) propionitrile.

(a) To a suspension of: 39.3 g (0.42 mole+10%) of $NaNO_3$ in 280 ml of concentrated $H_2SO_4$, 69.8 g (0.42 mole) of 2-(4'-chloro-phenyl) propionitrile were added in one hour between 0° and 5°. The cooling source was removed and the temperature allowed to rise to 25° followed by heating between 60° and 70° C. for one hour. The mixture was poured into ice water, extracted with ether, washed in water until neutral, and dried on $Na_2SO_4$. Evaporation of the ether produced an oil which crystallized rapidly. This solid was dispersed in diisopropyl ether, filtered with suction, rinsed with diisopropyl ether, and dried.

Melting pt.=89°–90° C. Yield=74.5 g=77% (theoretic yield=96 g).

Melting pt.=93°–94° C. [acetone—diisopropyl ether 1–2].

IR: $\nu$ C=O: 1650 cm⁻¹.

NMR (CDCl₃): 1.6 [d 3H CH₃]; 3.7 [q 1H CH₃—CH—]; 5.9 [s (D₂O) 2H—NH₂]; 7.5–7.9 [m 3H Ar]

| Weight analysis | C % | H % | Cl % | N % |
|---|---|---|---|---|
| Calculated | 47.27 | 3.97 | 15.51 | 12.26 |
| Experimental | 47.32 | 3.94 | 15.49 | 12.24 |

(b) A solution of 49.1 g (0.233 mole) of 2-(4'chloro-3'-nitro-phenyl) propionitrile was heated between 40° and 45° C. for 4 hours in 110 ml aqueous HCl, 36%. The mixture was poured into 3 liters of ice water and the nitrated amide was isolated according to a.

Melting pt.=92°–93° C. Yield=24.5 g=46% (theoretic yield=53.3 g).

EXAMPLE 2

2-(4'-amino-3'-nitro-phenyl) propionamide

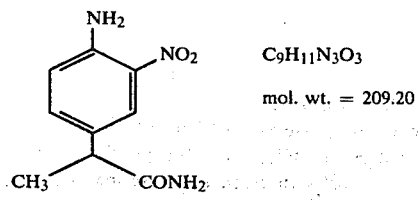

$C_9H_{11}N_3O_3$ mol. wt. = 209.20

A solution of 182.9 g (0.8 mole) of 2-(4'-chloro-3'-nitro-phenyl) propionamide, 895 ml (8.7 mole NH₄OH) ammonia, 34%, and 1600 ml ethanol were heated for 4 hours at 200° C.

Evaporation of the ethanol-water mixture furnished a solid which was dispersed in water, filtered with suction, rinsed with water then with diisopropyl ether, and dried. This solid was dissolved in 1400 ml ethanol and refluxed in the presence of Norit for 15 minutes. It was filtered, 1400 ml of water were added to the filtrate, and placed in the refrigerator for 1 hour. The precipitate formed was filtered with suction and dried.

Melting pt.=172°–173° C. Yield=89 g=53% (theoretic yield=167.5 g).

Melting pt.=173°–174° C. [C$_2$H$_5$OH - diisopropyl ether, 2.5-1].

IR $\nu$ NH$_2$: 3450-3400-3300 cm$^{-1}$ $\nu$ C=O: 1650 cm$^{-1}$.

NMR (DMSO$_{d6}$): 1.3 [d 3H CH$_3$—];

3.6 [q 1H CH$_3$—$\overset{|}{\text{CH}}$—]

6.9 [s 2H—CONH$_2$]; 7.4 [s (D$_2$O) 2H—NH$_2$]; 7.1 [d 1H Ar-5]; 7.5 [q 1H Ar-6]; 8 [d 1H Ar-2].

| Analysis    | C %   | H %  | N %   |
|-------------|-------|------|-------|
| Calculated  | 51.67 | 5.30 | 20.09 |
| Experimental| 51.72 | 5.34 | 20.03 |

EXAMPLE 3

2-(4'-amino-3'-nitro-phenyl) propionic acid

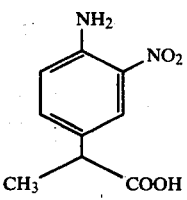

C$_9$H$_{10}$N$_2$O$_4$
mol. wt. = 210.19

A solution of 60.4 g (0.288 mole) of 2-(4'-amino-3'-nitro-phenyl) propionamide was refluxed for 1 hour in 300 ml 36% aqueous HCl. The solution was evaporated until dry and the pasty residue dissolved in 1000 ml of an aqueous solution of saturated sodium bicarbonate.

A small insoluble residue was eliminated by filtration, the filtrate was washed in ether and acidified (pH=1) by addition of 36% aqueous HCl. An oil was formed which crystallized rapidly. This solid was dissolved in 1500 ml of ether. After washing in water, then drying on Na$_2$SO$_4$ in the presence of Norit, evaporation of ether produced a yellow solid.

Melting pt.=125°–127° C. Yield=49.1 g=81% (theoretic yield=60.5 g).

Melting pt.=127°–129° C. [H$_2$O—C$_2$H$_5$OH 2.6-1].
IR $\nu$ NH$_2$: 3450-3350 cm$^{-1}$; $\nu$ C=O: 1700 cm$^{-1}$.
NMR (DMSO$_{d6}$) 1.4 [d 3H CH$_3$—];

3.8 [q 1H CH$_3$—$\overset{|}{\text{CH}}$—]

3.3–4.3 [signal blurred (D$_2$O) 1H—COOH]; 7.1 [d 2H Ar-5]; 7.4 [q 1H Ar-6]; 8 [d 1H Ar-2]; 7.3 [s (D$_2$O) 2H—NH$_2$].

EXAMPLE 4

2-(3'-nitro-4'-[1''-pyrrolyl]-phenyl) propionic acid

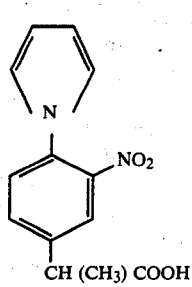

C$_{13}$H$_{12}$N$_2$O$_4$
mol. wt. = 260.25

49.1 g (0.233 mole) 2-(4'-amino-3'-nitro-phenyl) propionic acid and 33.9 g (0.233 mole+10%) 2,5-dimethoxytetrahydrofuran were refluxed for 15 minutes in solution in 700 ml of acetic acid. The solution was cooled and poured into ice water; an oil was precipitated which crystallized rapidly. This solid was filtered with suction and dissolved in ether. Evaporation of the ether after rinsing in water up to pH=7, then drying on Na$_2$SO$_4$, furnished an oil which was crystallized in hexane. The solid thus obtained was filtered with suction, then dried:

Melting pt.=114°–115° C. (softening at 110°). Yield=47.4 g=78% (Theoretic yield=60.6 g).

Melting pt.=115°–117° C. (diisopropyl ether).
IR $\nu$ C=O: 1700 cm$^{-1}$.
NMR (CDCl$_3$)

1.7 [d 3H—CH$_3$—$\overset{|}{\text{CH}}$ COOH] 3.9 [q 1H CH$_3$$\overset{|}{\text{CH}}$ COOH];

6.4 [m 2H pyrrole-3,4]; 6.8 [m 2H pyrrole-2,5]; 7.2–8 [m 3H phenyl]; 10.2 [s (D$_2$O) 1H- COOH].

| Analysis:   | C %   | H %  | N %   |
|-------------|-------|------|-------|
| Calculated  | 59.99 | 4.65 | 10.77 |
| Experimental| 60.03 | 4.67 | 10.72 |

EXAMPLE 5

2-[3'-amino-4'-(1''-pyrrolyl)-phenyl] propionic acid

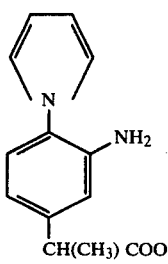

C$_{13}$H$_{14}$N$_2$O$_2$
mol. wt. = 230.26

(a) 14.5 g (0.056 mole) 2-[3'-nitro-4'-(1''-pyrrolyl)-phenyl] propionic acid were hydrogenated under pressure at 25° C. in solution in 300 ml methanol and in the presence of 3.5 g (10% palladium on charcoal. The theoretical pressure drop is reached in the space of 1 hour. The product is isolated by evaporating the filtrate obtained after elimination of the catalyst: it is in the form of a colorless crystallized solid which is dispersed in hexane, filtered with suction, washed with hexane, and dried.

Melting pt.=119°-123° C. Quantity=11.4 g.

These 11.4 g of solid were purified by chromatography in a silica gel column (about 150 g) using chloroform as the eluent:

Melting pt.=121°-128° C. Quantity=9.5 g.

After recrystallization in an isopropanol-hexane mixture (1-2),

Melting pt.=126°-128° C. Yield: 5.4 g=42% (theoretic yield=13 g).

(b) This reduction can also be carried out at normal pressure between 30° and 35° C. using 2 g 10% palladium on charcoal and 200 ml methanol for 10 g of nitrated derivative to be hydrogenated.

In this case, the adsorption time is about 3 hours:

Melting pt.=125°-126° C. Yield=7.6 g=86%. (theoretic yield=8.85 g).

Melting pt.=130°-132° C. ($C_2H_5OH$).

IR: $\nu$ $NH_2$: 3390-3310 cm$^{-1}$; $\nu$ C=O: 1710 cm$^{-1}$.

NMR ($CDCl_3$) 1.5 [d 3H $CH_3$—]; 3.7

$$[q\ 1H\ CH_3\ \overset{|}{CH}\ COOH];$$

6.4 [m 2H pyrrole-3,4, 2H—$NH_2$ ($D_2O$), 1H—COOH ($D_2O$)]; 6.8-7.4 [m 2H pyrrole-2,5, 3H phenyl].

| Analysis: | C % | H % | N % |
|---|---|---|---|
| Calculated | 67.80 | 6.13 | 12.17 |
| Experimental | 67.98 | 6.16 | 12.06 |

It will be obvious to those skilled in the art that various changes may be made without departing from the scope of the invention and the invention is not to be considered limited to what is described in the specification.

What is claimed is:

1. A substituted arylaliphatic acid represented by the formula

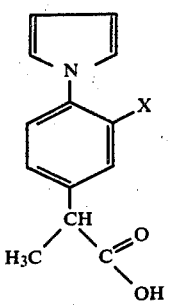

in which X is a nitro or amino group.

2. A compound in accordance with claim 1, wherein X is amino.

3. A pharmaceutical composition comprising a substituted arylaliphatic acid in accordance with claim 1 as the active principle, in an analgesic or anti-inflammatory amount and a pharmaceutically acceptable excipient.

4. A pharmaceutical composition in accordance with claim 3, in the form of a tablet with 100 mg of active principle.

5. A composition in accordance with claim 3, wherein X is amino.

6. A method of treating patients with pain or inflammation comprising orally administering to the patient an analgesic or anti-inflammatory amount of the arylaliphatic acid of claim 1.

7. A method of treating patients with pain or inflammation comprising orally administering to the patient an analgesic or anti-inflammatory amount of the composition of claim 3.

8. A method in accordance with claim 7, wherein said composition is administered at a daily dose of 200-600 mg of active principle.

* * * * *